United States Patent
Levine

(10) Patent No.: US 6,503,248 B1
(45) Date of Patent: Jan. 7, 2003

(54) COOLED, NON-STICKING ELECTROSURGICAL DEVICES

(75) Inventor: Andy Levine, Newton Center, MA (US)

(73) Assignee: Seedling Enterprises, LLC, Newton, MA (US)

( * ) Notice: Subject to any disclaimer, the term of this patent is extended or adjusted under 35 U.S.C. 154(b) by 0 days.

(21) Appl. No.: 09/702,006

(22) Filed: Oct. 30, 2000

(51) Int. Cl.$^7$ ............................................... A61B 18/14
(52) U.S. Cl. ........................... 606/45; 606/48; 606/49; 606/51
(58) Field of Search ..................... 606/41, 42, 45, 606/46, 48–52; 607/105

(56) References Cited

U.S. PATENT DOCUMENTS

| | | | |
|---|---|---|---|
| 3,496,942 A | 2/1970 | Shipley | 128/401 |
| 3,929,136 A | 12/1975 | Kreeb et al. | 128/303.1 |
| 3,991,764 A | 11/1976 | Incropera et al. | 128/303.1 |
| 4,074,718 A | 2/1978 | Morrison, Jr. | 128/303.14 |
| 4,202,336 A | 5/1980 | van Gerven | 128/303.1 |
| 4,492,231 A | 1/1985 | Auth | 128/303.17 |
| 4,532,924 A | 8/1985 | Auth et al. | 128/303.17 |
| 4,674,499 A | 6/1987 | Pao | 128/303.14 |
| 4,931,047 A | 6/1990 | Broadwin et al. | 604/22 |
| 5,171,311 A | 12/1992 | Rydell et al. | 606/48 |
| 5,197,963 A | 3/1993 | Parins | 606/46 |
| 5,230,349 A | 7/1993 | Langberg | 128/786 |
| 5,234,004 A | 8/1993 | Hascoet et al. | 607/116 |
| 5,282,799 A | 2/1994 | Rydell | 606/48 |
| 5,318,589 A | 6/1994 | Lichtman | 606/205 |
| 5,334,193 A | 8/1994 | Nardella | 606/41 |
| 5,342,357 A | 8/1994 | Nardella | 606/40 |
| 5,348,554 A | 9/1994 | Imran et al. | 606/41 |
| 5,417,686 A | 5/1995 | Peterson et al. | 606/25 |
| 5,437,662 A | 8/1995 | Nardella | 606/40 |
| 5,647,871 A | 7/1997 | Levine et al. | 606/45 |
| 5,908,418 A | 6/1999 | Dority et al. | 606/40 |
| 5,925,039 A | 7/1999 | Landingham | 606/41 |
| 6,056,747 A | 5/2000 | Saadat et al. | 606/50 |
| 6,074,389 A | 6/2000 | Levine et al. | 606/45 |
| 6,287,305 B1 * | 9/2001 | Heim et al. | 606/41 |

FOREIGN PATENT DOCUMENTS

| | | |
|---|---|---|
| AU | 120788 | 1/1946 |
| EP | 0 246 350 A1 | 11/1987 |
| EP | 0480639 A2 | 4/1992 |
| EP | 0 761 174 A1 | 3/1997 |
| NL | 1 004 655 | 3/1998 |
| WO | WO 98/53750 | 12/1998 |
| WO | WO 01/15615 A1 | 3/2001 |

OTHER PUBLICATIONS

Brochure on Seitzinger Tripolar™ Cutting Forceps, Cabot Technology Corp., 1994, consisting of three pages.

Holman, J.P., *Heat Transfer*, Fourth Edition, McGraw–Hill Book Company, pp. 464–467.

Hoffmann, E., et al., "Temperature–controlled radiofrequency catheter ablation of AV conduction: first clinical experience," *European Heart Journal*, 14:57–64, (1993).

Bart, S.F., et al., "The Mechanism of Electrosurgical Coagulation: Steam Evolution Versus Dielectric Breakdown," *IEEE*, pp. 297–300, (1985).

Neiman, T.S., et al., "Thermal Characterization of Electrosurgery," *Biomat., Med. Dev., Art. Org.*, 11(1) :93–101, (1983).

* cited by examiner

*Primary Examiner*—Lee Cohen
(74) *Attorney, Agent, or Firm*—Hamilton, Brook, Smith & Reynolds, P.C.

(57) ABSTRACT

An electrosurgical device has an electrode and a heat pipe to conduct heat from the electrodes where substantially all heat conducted from the electrode through the heat pipe is dissipated along the length of the heat pipe. The heat pipe can have a thermal time constant less than 60 seconds and preferably less than 30 seconds.

16 Claims, 6 Drawing Sheets

COOLED, NON-STICKING ELECTROSURGICAL DEVICES

BACKGROUND OF THE INVENTION

Electrosurgery is commonly used to cauterize, cut and/or coagulate tissue. In typical electrosurgical devices, RF electrical energy is applied to the tissue being treated. Local heating of the tissue occurs, and, depending upon the waveform of the applied energy and the electrode geometry, the desired effect is achieved. By varying the power output and the type of electrical waveform, it is possible to control the extent of heating and, thus, the resulting surgical effect. For example, a continuous sinusoidal waveform is best suited for cutting, while a waveform having periodically spaced bursts of a partially rectified signal produces coagulation.

In bipolar electrosurgery, the electrosurgical device includes two electrodes. The tissue being treated is placed between the electrodes, and the electrical energy is applied across the electrodes. In monopolar electrosurgery, the electrical excitation energy is applied to a single electrode at the surgical site, and a grounding pad is placed in contact with the patient. The energy passes from the single monopolar electrode through the tissue to the grounding pad.

While tissue heating is the mechanism by which the various surgical treatments are realized, it can also cause various obstacles to optimum procedure performance. For example, as the heat causes tissue fluids to evaporate. As the tissue is desiccated, the electrical resistance of the tissue increases, making it increasingly more difficult to supply adequate power to the tissue. Eventually, the resistance rises to such a high level that it is impossible to continue the procedure. This is such a well-known and common problem in prior electrosurgical devices that surgeons have become accustomed to it and have tailored their procedures to minimize its effects. Typically, surgeons operate prior electrosurgical devices at a very low power level. This prevents the electrode and the adjacent tissue from becoming too hot too fast. Unfortunately, it also requires the surgeon to perform the procedure much more slowly than he would if he could operate the device at full power. As a result, the procedure takes much longer, requiring more operating room time and longer exposure of the patient to dangerous anesthetics.

Heating also causes charring of the tissue. Like desiccated tissue, charred tissue is of very high resistance. Therefore, as the surface of the tissue being treated becomes charred, it becomes difficult, and eventually impossible, to continue delivering power to the tissue as desired. Once again, to avoid the problem, surgeons perform procedures much more slowly than is desirable.

Electrosurgical procedures are also hindered by adherence of tissue to heated electrodes. During electrosurgery, the heated tissue tends to transfer heat to the electrodes. As an electrode becomes hot, tissue tends to stick to it, resulting in various complications. First, the tissue stuck to the electrode can have a high resistance and can therefore hinder delivery of power to the tissue. In prior devices, while performing a procedure, a surgeon must periodically remove the device from the patient and clean it before continuing. In addition, surgeons can perform the procedure at reduced power settings to reduce tissue adherence and thus the frequency of cleanings.

Tissue sticking can also cause unnecessary bleeding. During electrosurgical procedures, the tissue being treated often heats the electrode such that, when the electrode is removed from the tissue, a portion of the tissue sticks to the electrode and is torn away, which likely results in bleeding. Thus, as the surgeon is attempting to cauterize in order to stop bleeding, he is actually causing more bleeding. He must therefore make repeated attempts to cauterize the area, first cauterizing, then tearing away tissue, then recauterizing the torn tissue, etc. Once again, in an attempt to alleviate the problem, surgeons will typically operate at low power, resulting in a procedure requiring much more time to complete than is desirable.

Another problem caused by heated electrodes is the creation of smoke in the proximity of the surgical site. As a result, the surgeon's visibility is reduced, and he must periodically interrupt the procedure to allow the smoke to dissipate.

It has been recognized that cooling the surgical site during electrosurgery would be desirable. In response, systems have been developed which flush the surgical site with fluid during surgery. However, this results in much more steam being created at the surgical site and the associated reduction in visibility. Also, the fluid introduced at the site must be aspirated as the procedure is performed.

U.S. Pat. No. 5,647,871 introduced a high conductivity device, a heat pipe, to conduct heat from the heated electrode to a heat sink. The heat sink maintains the heat pipe temperature below 80° C., the sticking point of tissue to metal.

SUMMARY OF THE INVENTION

It has been determined that for certain heat pipe diameters and lengths, the heat pipe itself can store and transfer sufficient heat to the environment, without the use of an additional heat sink, to maintain its temperature below the required 80° C.

There are several advantages to using the heat pipe to dissipate heat, rather than using a heat sink. First, elimination of the heat sink makes the device more compact, less expensive and therefore practical for sale. Second, the ideal electrosurgical pencil device would operate between 60 and 80° C. The lower temperature is the initiation of coagulation and the upper temperature is the sticking point. The addition of the heat sink lowers the operating temperature of the heat pipe which can negatively affect the depth of penetration of the thermal effect. If the pencil tip is too cold, then there may be a delay in the onset of coagulation and the effect of the coagulation will be deeper in the tissue than may be desired. The present invention passively controls the temperature of the pencil so that the temperature remains closer to the desired set point. Also, the addition of a heat sink adds thermal inertia to the device. This slows the rise time of the heat pipe temperature and also slows the drop in temperature after energy application is stopped. Both of these situations are undesirable. Removal of heat sink removes the thermal inertia.

The invention relates to an electrosurgical device having an electrode and a heat pipe for conducting heat from the electrode. Substantially all heat conducted from the electrode through the heat pipe is dissipated along the length of the heat pipe. The distal end of the heat pipe includes an outer surface having a nickel plated layer or a gold plated layer. The heat pipe is covered along its length by a sheath. The sheath can be formed of a heat shrink tubing. The heat pipe can be attached to and extend from a handle.

The heat pipe has a surface area between approximately 11.0 cm$^2$ (1.71 in$^2$) and 15.0 cm$^2$ (2.33 in$^2$). The heat pipe also includes a diameter of 3 mm (0.12 inches) and a length between approximately 9 cm (3.5 inches) and 11.5 cm (4.5 inches). The heat pipe has a thermal time constant less than 60 seconds and preferably has a thermal time constant less than 30 seconds.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
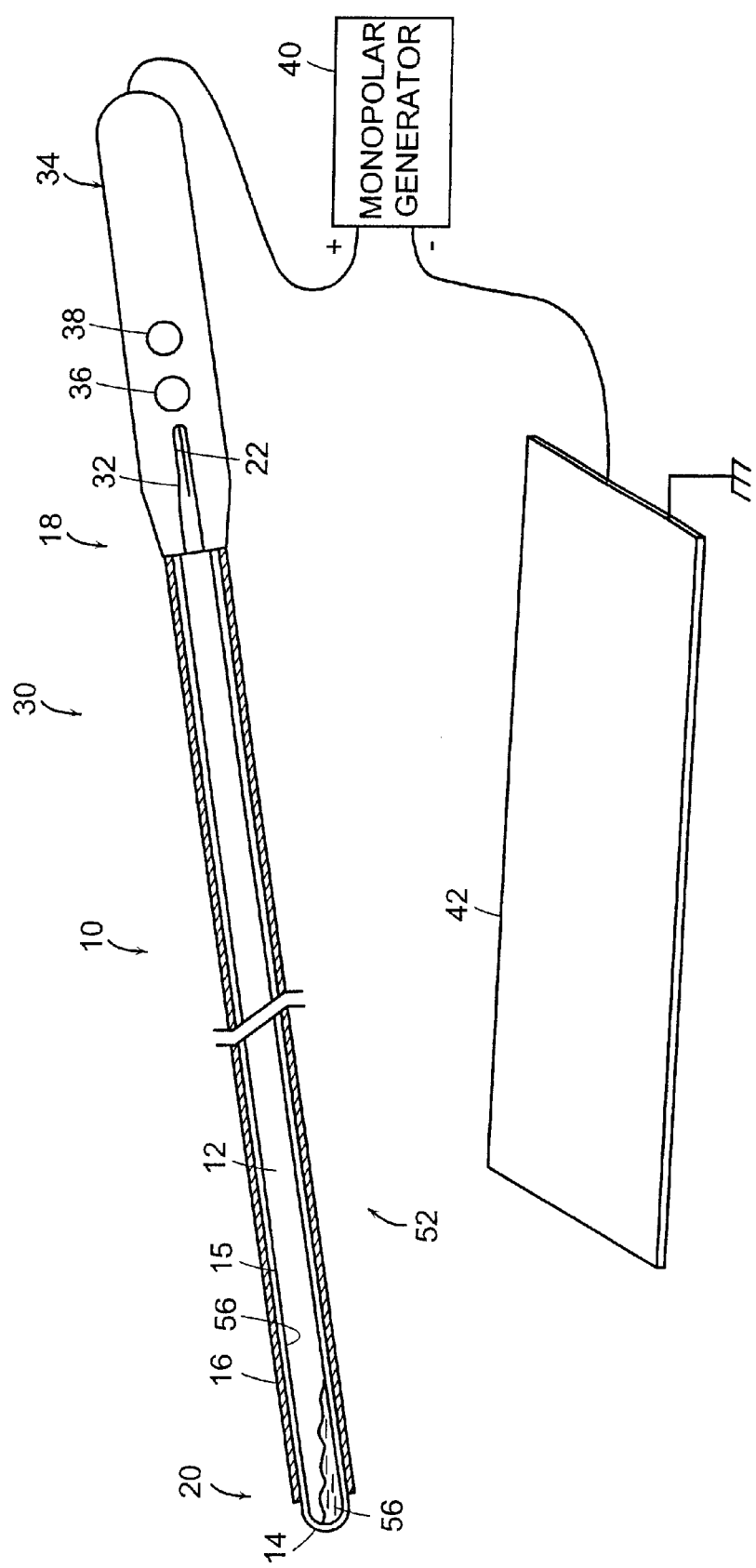
FIG. 1 shows heat pipe mounted to a handle.

FIG. 1 schematically depicts an embodiment of a monopolar electrosurgical system 30 in accordance with the present invention. In this embodiment, the monopolar probe or electrosurgical device 52 employs a heat pipe heat transfer device 10 as the monopolar electrode. The heat pipe is a well-known heat transfer mechanism and is described in textbooks on heat transfer such as *Heat Transfer*, Fourth Edition, by J. P. Holman, McGraw-Hill, 1963, pp. 464–467, which is incorporated herein in its entirety by reference.

Referring to FIG. 1, the heat pipe 10 includes an internal cavity 12 which is sealed at both ends. The cavity 12 is partially evacuated and contains a heat transfer fluid such as water 56. The outer shell 15 can be made of a conductive metallic material such as copper. The shell 15 can be covered over most of its length by an electrically insulating cover or sheath 16. The exposed distal end 20 of the heat pipe 10 is coated with a conductive non-toxic material such as gold or nickel, for example, which forms an outer surface 14. Preferably, the distal end 20 is first nickel plated, then gold plated.

The proximal end 18 of the heat pipe 10 includes a male connector 22 and is in conductive contact with a receptacle 32 of the pencil or handle 34. As with the previously described monopolar instruments, the male connector 22 is inserted into the receptacle 32 of the handle 34. When electrical energy is applied to the male connector 22, the energy is conducted along the conductive outer shell 15 of the heat pipe 10 to the distal end 20 of the heat pipe 10. The distal end 20 serves as a monopolar electrode of the device. The distal end 20 can be a ball end or can be a tapered end, for example.

In operation, the electrode 26 is placed adjacent to tissue being treated. At the same time, the patient is maintained in contact with a grounding pad 42. The pencil 34 controls application of the electrical energy. One of the pushbuttons 36 and 38 can be depressed to apply the electrical energy to the tissue according to the desired tissue treatment. Typically, one of the buttons 36 applies a coagulation waveform to the heat pipe 10 to coagulate tissue while the other button 38 causes a cutting waveform to be applied to the tissue. When one of the buttons is pressed, electrical energy from a monopolar generator 40 is applied across the electrode 20 and the grounding pad 42 to treat the tissue.

The heat pipe 10 of the probe 52 serves to cool the monopolar electrode 20. During operation, the distal end electrode 20 is heated by the tissue. In accordance with the well-known operation of the heat pipe heat transfer device 10, the water 56 within the cavity 12 of the heat pipe 10 evaporates, and the cavity 12 fills with vapor. The inner wall 56 of the heat pipe 10 serves as a wick, which, in one embodiment, takes the form of multiple grooves or slots distributed over the entire inner wall 56 of the outer shell 15. At the proximal end 18 of the device 52, the vapor condenses, and the resulting liquid flows back to the distal end of the device via capillary action within the wick 56. Heat is thus carried away from the electrode 20 at the distal end of the device.

The heat pipe 10 itself is used as a heat exchanger to dissipate heat formed in the heat pipe. During operation, the distal end electrode 20 is heated by the tissue. Heat from the surgical site can flow from the distal end 20 of the heat pipe 10 to the proximal end 18 of the heat pipe 10 and can be dissipated along the length of the heat pipe 10 to cool the entire heat pipe 10, thereby maintaining the electrode at a temperature below 80° C.

The heat pipe 10 can also have a diameter of 3 mm (0.12 inches). For a 3 mm diameter heat pipe 10 having a sheath 16 with insulation 1 mm thick (4 mm diameter overall), the optimal length of this design is between 9 cm (3.5 inches) and 11.5 cm (4.5 inches). Based on experimentation, a heat pipe length shorter than this range does not provide sufficient length or area to transfer the heat. A heat pipe length longer than this range does not provide a sufficient temperature. The optimal length of larger diameter heat pipes will be shorter, and smaller diameter heat pipes will be longer.

The heat transfer area for a cylinder is $\pi DL$. Based on the above dimensions, the ideal surface area for heat transfer for this device is between 11.0 cm$^2$ (1.71 in$^2$) and 15.0 cm$^2$ (2.33 in$^2$). This area can be obtained through many combinations of length, diameter and surface geometry. For example, the heat transfer area can be increased by adding serrations or fins around the outside of the tube. If this is done, shorter or smaller diameter heat pipes 10 can be made to work.

The distal end of the heat pipe can be shaped to form any desired electrode shape such as the spatula, L-hook, and J-hook. The heat pipe configuration can also be used in bipolar instruments. The monopolar instrument is shown in FIG. 1 for illustration purposes only and is not intended to be a limitation. The heat pipe can also be formed having a non-circular cross section. For example, the heat pipe can have an oval-shaped cross section.

Figure 2:
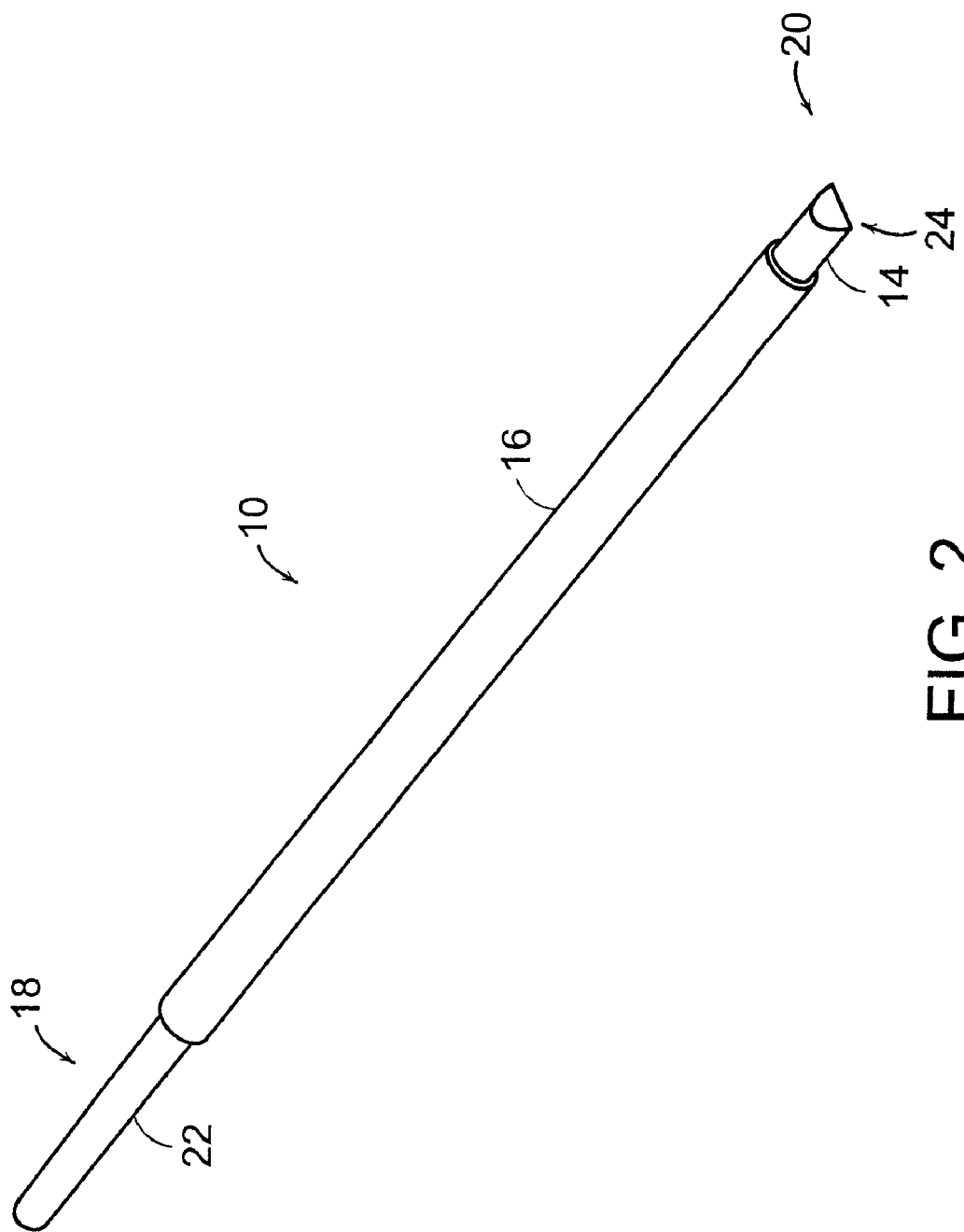
FIG. 2 illustrates a perspective view of an alternate heat pipe and electrode used in the present invention.
Figure 3:
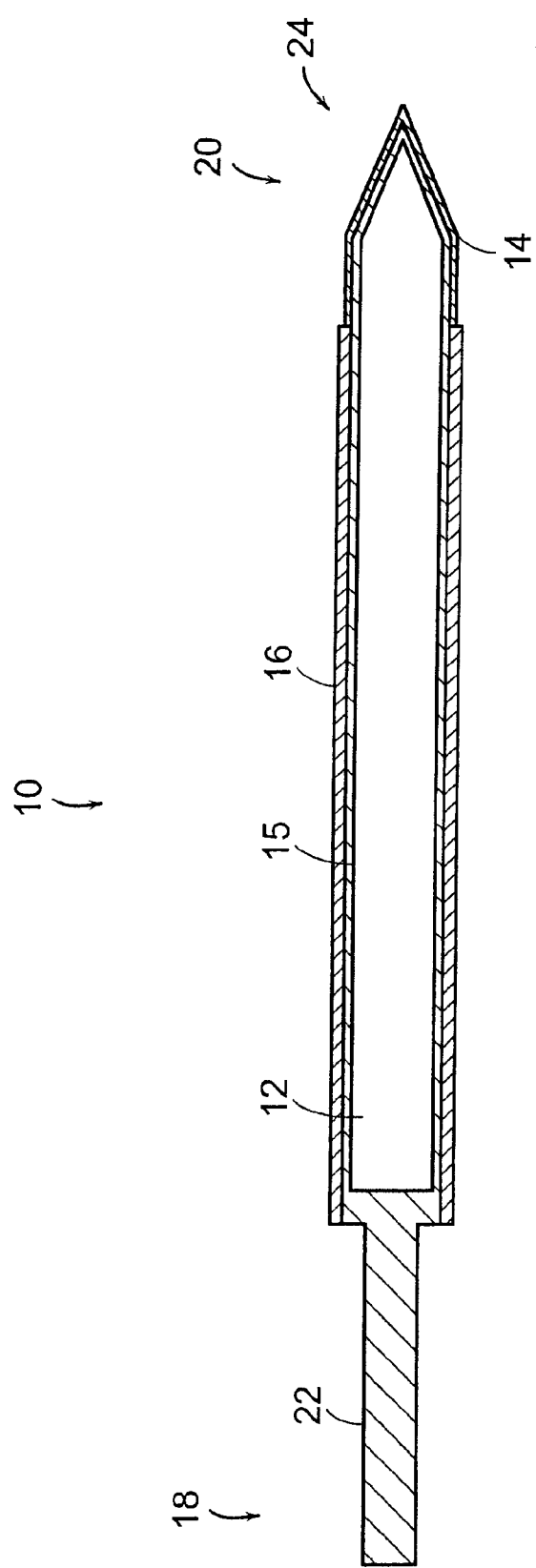
FIG. 3 illustrates a cross-sectional view of the heat pipe of FIG. 2.

FIGS. 2 and 3 show an embodiment of a heat pipe 10. The heat pipe 10 includes an outer metal shell 15, a cavity 12, and a sheath 16. The outer shell 15 transfers electrical energy from a generator to a surgical site. An outer electrode can be a gold plated surface, for example. The sheath 16 can be heat shrink tubing, for example, and can electrically insulate the outer shell 15 of the heat pipe 10.

The heat pipe 10 can include a proximal end 18 and a distal end 20. The proximal end can be swaged at 22 for insertion within a handle of an electrosurgical device from which electrical power is obtained. The distal end 20 can be crimped to provide a tapered end 24, as shown in FIG. 3. The tapered end 24 allows a user to focus energy to a surgical site to produce a cutting effect. The tapered end 24 also allows a user to concentrate the cutting to a particular area of tissue.

It has been shown in the literature that many of the effects caused by heated electrodes can be avoided if the temperature at the electrode-tissue interface is maintained below a temperature of about 80° C. (See "Temperature-Controlled Radio Frequency Catheter Ablation of AV Conduction: First Clinical Experience," by Hoffmann et al., *European Heart Journal* (1993) 14,pages 57–64.) The present invention can maintain that electrode temperature during any of the various procedures performed. Electrode temperature is maintained by dissipating heat along the length of the heat pipe 10 rather than by utilizing a heat sink attached to the heat pipe 10.

At low heat fluxes, the heat pipe is essentially an isothermal device. Therefore, as heat is input to one end, touching the tissue, the heat is rapidly distributed throughout the heat pipe, raising its temperature almost uniformly. Because the heat is uniformly distributed along the length of the device, the entire length of the device is available to convect the heat to the ambient air. If there is sufficient area of the heat pipe exposed to the ambient air, there is no need to store the heat in a heat sink at one end of the device.

A heat balance occurs in the heat pipe when heat coming into the heat pipe from the tissue raises the temperature of the heat pipe. As its temperature rises, the heat pipe convects heat to the ambient air. In the steady state, the heat entering the tip is equal to the heat convected to the ambient air.

Figure 4:
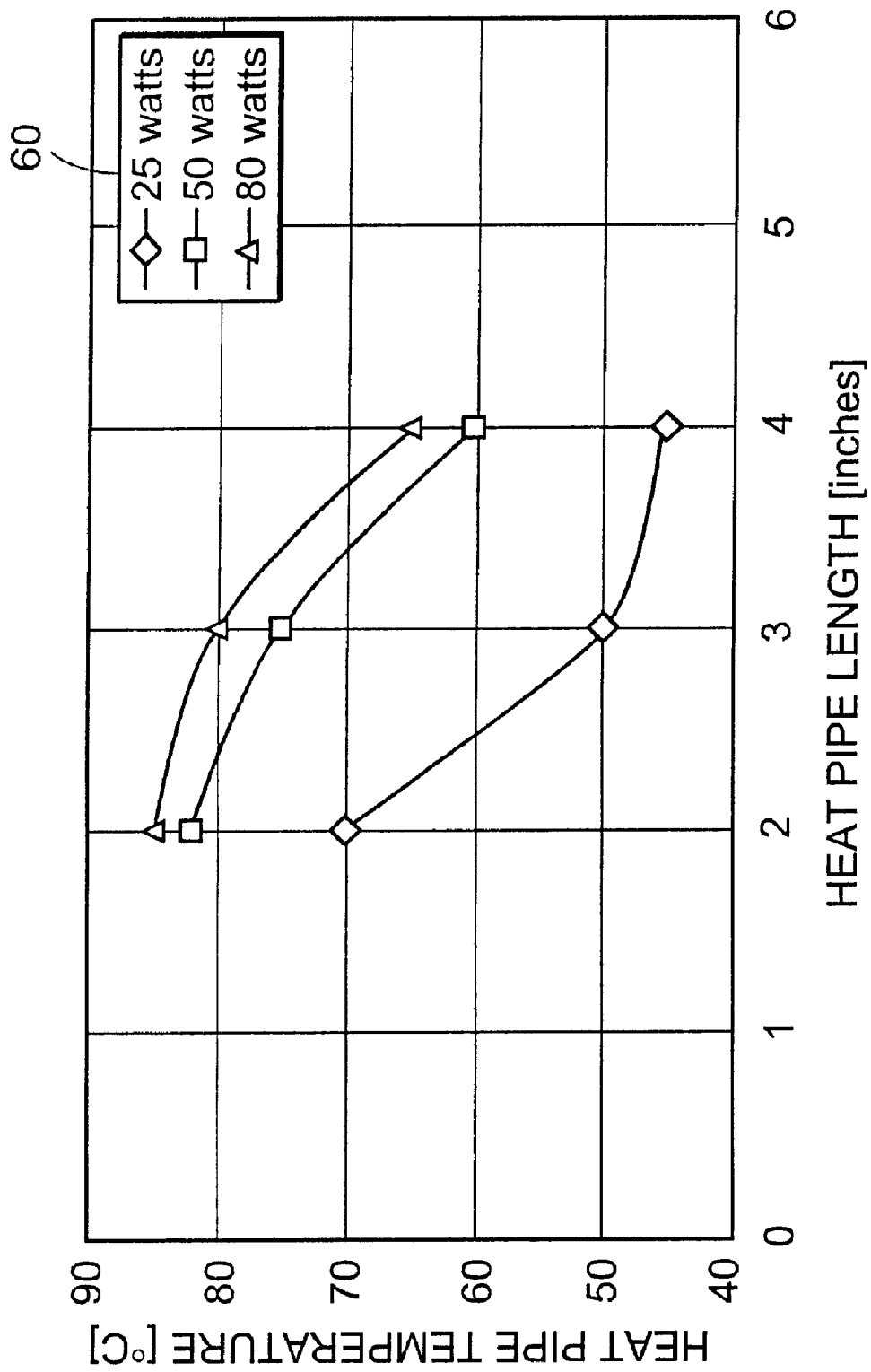
FIG. 4 shows a graph illustrating experimentally measured variation of heat pipe temperature as a function of heat pipe length and input power.

A relationship exists between heat pipe length and steady state temperature or heat balance. The heat pipe can be sized to obtain a desired steady state temperature. FIG. 4 illustrates the relationship between heat pipe temperature, heat pipe length and input power. As shown from experimental data, the shorter the length of the heat pipe, the greater the steady state temperature of the heat pipes for any given power input to the tissue. The various power input levels used in the experiments are shown in legend 60. This relation exists because the area for convection is reduced as the length of the heat pipe is decreased.

The heat entering the heat pipe due to tissue heating is largely unknown and can vary depending upon the type of tissue being heated. Experiments were conducted such that for a room temperature heat pipe (ie: one with a large heat sink attached), the heat transfer from cauterized tissue was measured as approximately 1.2–1.5 watts, depending upon the generator output. If, however, the heat pipe temperature is allowed to rise, less heat can conduct to the heat pipe since the temperature gradient between the heat pipe and the tissue is reduced.

The relation between heat pipe length and the steady state temperature of the heat pipe has also been determined using mathematical modeling techniques. The following is a mathematical model of the heat transfer from the heat pipes, as modeled by natural convection from a horizontal cylinder with a constant heat flux. The natural convection heat transfer from any object to an ambient sink is defined as:

$$Q = h A (T_w - T_{amb})$$

Solving for the heat pipe wall temperature:

$$T_w = \frac{Q}{h \pi D x} + T_{amb}$$

This equation is used to determine the heat pipe temperature ($T_w$) for various heat fluxes and heat pipe lengths.

Next the heat transfer coefficient h must be determined and is defined in terms of the dimensionless Nusselt number, a length and the thermal conductivity of the sink medium:

$$Nu_x = \frac{hx}{k}$$

The Nusselt number for a horizontal cylinder taken from J. P. Holman, "Heat Transfer", 1976, McGraw-Hill p. 250, herein incorporated by reference:

For $10^{-5} < GrPr < 10^{12}$

For $10^{-5} < GrPr < 10^{12}$ $$Nu_x = \left(0.6 + 0.387 \left(\frac{Gr_x Pr}{(1 + (0.559/Pr)^{9/16})^{16/9}}\right)^{1/6}\right)^2$$

The Grashoff number is defined as:

$$Gr_x = \frac{g \beta (T_w - T_{amb}) x^3}{v^2}$$

Figure 5:
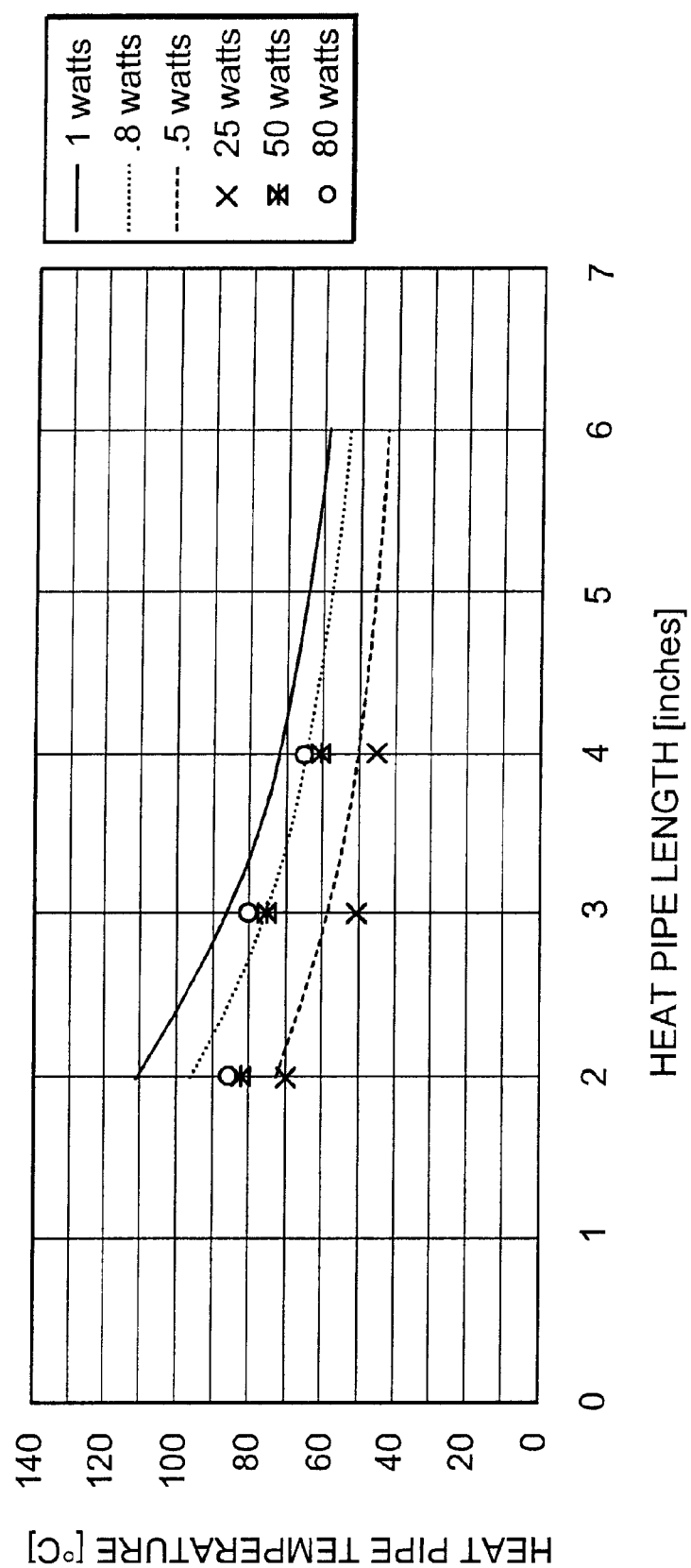
FIG. 5 illustrates a comparison of the experimentally measured data of FIG. 4 and the mathematically determined relationship between heat pipe length, temperature and input power.

Using these natural convection equations, the predicted wall temperatures were calculated for several heat pipe lengths and power inputs illustrated in FIG. 5. This natural convection analysis confirms the experimentally determined data as also shown in FIG. 5. The data lines represent the mathematical model results at heat fluxes through the heat pipe of 0.5, 0.8 and 1 watt. The data points are data from the experimental testing at generator outputs of 25, 50 and 80 watts as seen in FIG. 4.

The mismatch between the model and the data at high temperatures (short heat pipes) can be because, as the heat pipe heats up significantly, the amount of heat conducted from the tissue should drop, making the actual heat pipe temperature drop as well. This was not accounted for in this analysis.

The mathematical and experimental analysis shows that by varying the length of the heat pipe without a specific heat sink attached to it, the steady state temperature of the heat pipe can be varied and therefore controlled. This cannot be done if a large heat sink is placed on one end of the heat pipe.

Another factor that can determine the optimal electrosurgical system is the vapor pressure inside the heat pipe. Current heat pipes are at a vacuum such that the water within the heat pipe vaporizes at temperatures below room temperature. The heat pipe can have a vapor pressure of approximately 60° C. In this way, the heat pipe can rapidly heat up to 60° C., and then remain at that temperature during use.

A thermally conductive sheath can also be used to cover the rod of the heat pipe. The thermally conductive sheath can increase the amount of heat transferred from the pipe to the atmosphere and can result in a pipe having a shorter length.

Figure 6:
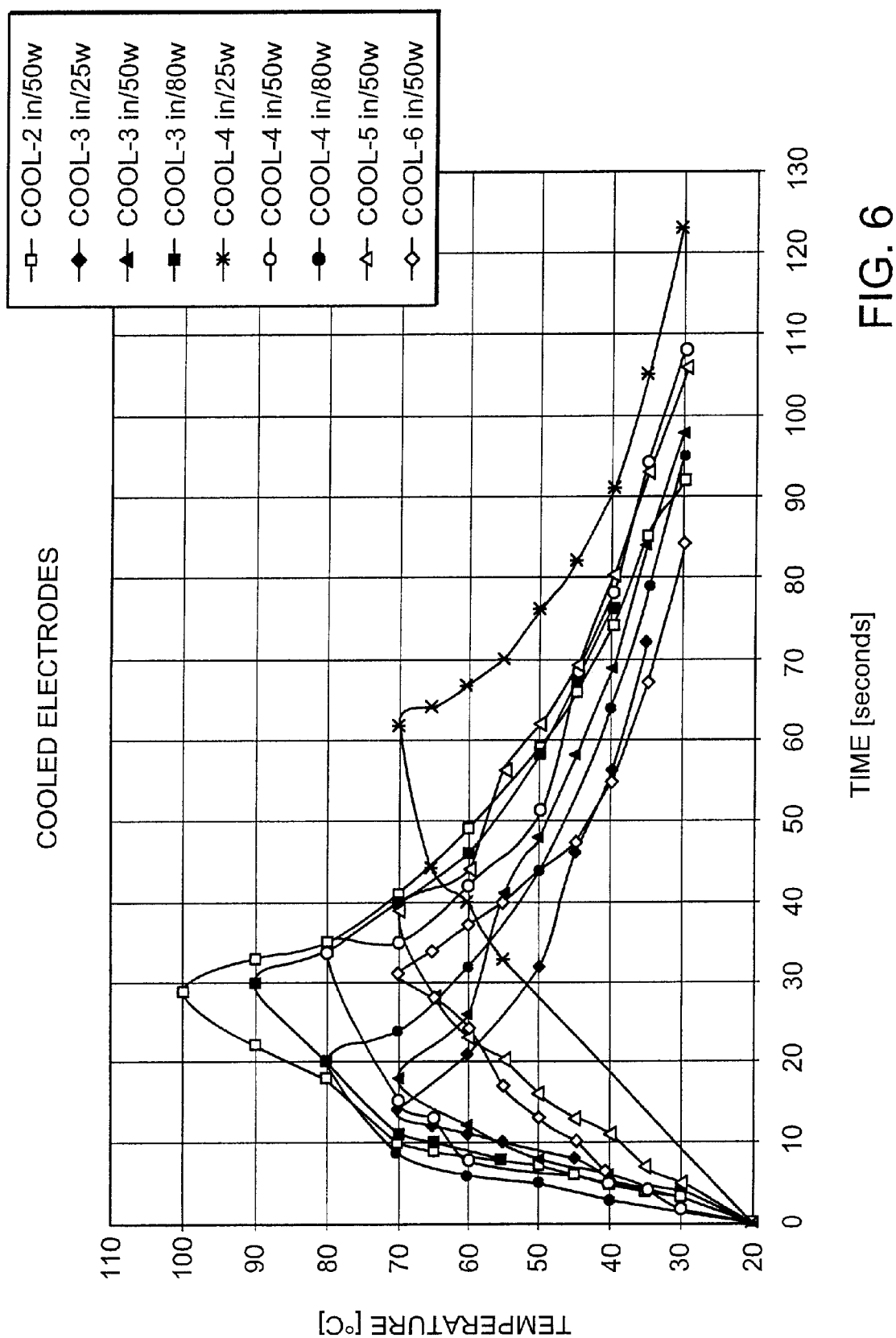
FIG. 6 shows the thermal time constants for varying length heat pipes with varying input wattages.

FIG. 6 illustrates the heat-up transients or thermal time constants for the heat pipe designs. The graph shows that on average, the steady state temperature is reached within 30 seconds and always within 60 seconds. This is due to the small thermal mass of the heat pipes. In practice, it is preferred that the thermal time constant of the heat pipe 10 be less than 60 seconds and preferably less than 30 seconds.

In contrast, testing was performed with the heat pipes used to produce FIG. 6, having aluminum heat sinks mounted to their ends in the handles. The temperatures of these devices rose slowly, at roughly 4–5° C. per minute. This is obviously much slower than the 50–60° C. per 30 seconds seen in FIG. 6. By providing adequate heat transfer area, the thermal mass of the device can be minimized thereby permitting the heat pipe to heat up rapidly, and reach its steady state temperature.

While this invention has been particularly shown and described with references to preferred embodiments thereof, it will be understood by those skilled in the art that various changes in form and details may be made therein without departing from the scope of the invention encompassed by the appended claims.

What is claimed is:

1. An electrosurgical device comprising:

an electrode; and a heat pipe for conducting heat from the electrode, substantially all heat conducted from the electrode through the heat pipe being dissipated along the length of the heat pipe.

2. The electrosurgical device of claim 1 wherein the electrode comprises an outer surface having a nickel plated layer.

3. The electrosurgical device of claim 1 wherein the electrode comprises an outer surface having a gold plated layer.

4. The electrosurgical device of claim 1 wherein the heat pipe comprises a sheath.

5. The electrosurgical device of claim 4 wherein the sheath comprises heat shrink tubing.

6. The electrosurgical device of claim 1 wherein the heat pipe has a thermal time constant less than 60 seconds.

7. The electrosurgical device of claim 1 wherein the heat pipe has a thermal time constant less than 30 seconds.

8. The electrosurgical device of claim 1 wherein the heat pipe comprises a surface area between approximately 11.0 $cm^2$ and 15.0 $cm^2$.

9. The electrosurgical device of claim 1 wherein the heat pipe comprises a diameter of about 3 mm and a length between approximately 9 cm and 11.5 cm.

10. The electrosurgical device of claim 1 wherein the heat pipe extends from a handle.

11. The electrosurgical device of claim 1 in a bipolar instrument.

12. A method for using an electrosurgical device comprising:

providing an electrosurgical device having an electrode and a heat pipe for conducting heat from the electrode;

placing the electrode against a surgical site;

applying electrical power to the electrode to heat the surgical site; and dissipating heat from the electrode through the heat pipe, substantially all heat conducted from the electrode through the heat pipe being dissipated along the length of the heat pipe.

13. The method of claim 12 further comprising cauterizing a surgical site.

14. The method of claim 12 further comprising cutting a surgical site.

15. The method of claim 12 further comprising coagulating a surgical site.

16. The method of claim 12 further comprising supplying the electrical energy through bipolar electrodes.

* * * * *